United States Patent [19]
Ribeiro

[11] Patent Number: 5,165,647
[45] Date of Patent: Nov. 24, 1992

[54] EQUIPMENT FOR HOLDING A SERUM CONTAINER

[76] Inventor: Jose P. Ribeiro, rua Matias Cardoso, No. 11 - Apto. 205, Belo Horizonte, Minas Gerais, Brazil

[21] Appl. No.: 718,998

[22] Filed: Jun. 21, 1991

[30] Foreign Application Priority Data

Jun. 25, 1990 [BR] Brazil .................................. 7001140
Aug. 24, 1990 [BR] Brazil .................................. 7001702

[51] Int. Cl.⁵ ............................................. A47H 1/10
[52] U.S. Cl. .................................... 248/323; 248/333; 403/59; 403/164
[58] Field of Search ............... 248/323, 333, 298, 237, 248/289.1, 296, 287, 307; 362/404, 419; 128/DIG. 26; 604/32; 403/164, 165, 78, 59, 61

[56] References Cited

U.S. PATENT DOCUMENTS

| 3,305,281 | 2/1967 | Dumpis | 403/164 X |
| 3,944,180 | 3/1976 | Rogers | 248/323 |
| 4,240,660 | 12/1980 | Roth et al. | 248/323 X |
| 4,309,121 | 1/1982 | Salame | 403/164 |
| 4,580,754 | 4/1986 | Hughes | 248/323 X |

*Primary Examiner*—Ramon O. Ramirez
*Attorney, Agent, or Firm*—Anthony A. O'Brien

[57] ABSTRACT

Equipment for a holding serum container is disclosed as including a vertical stem having in its lower end a hook to hold a serum container, the stem being horizontally displaceable by means of a slider which travels within a rotatable tubular structure linked to a hanger to eventually rotate the equipment which may be fixed to a room or vehicle ceiling.

4 Claims, 3 Drawing Sheets

EQUIPMENT FOR HOLDING A SERUM CONTAINER

BACKGROUND OF THE INVENTION

The present invention relates to equipment for holding a serum container and the like and, more particularly, to such equipment having a support as is found in hospitals, sick rooms, etc.

The conventional support for a serum container includes a vertical rod on a tripod forming a fixed structure to a bed or the like which cannot follow a patient's movements in bed unless the patient has the supervision of a nurse or other attendant. In addition, the fixed structure occupies a critical area near the patient and thus has to handled with extreme care to avoid accidents; even a minor accident could result in the risk of contanination among patients.

OBJECTS OF THE INVENTION

It is an object of the present invention to substantially reduce the risk of contanimation from accidents involving a broken serum container.

Another object of this invention is to fix a serum container support to the ceiling of a room, vehicle or the like, which support permits movement of the serum container without being unfixed to the ceiling.

This invention has a further object in that a mounting structure permits movement of a serum container or the like relative to an overhead support without being hampered by underhead arrangements.

SUMMARY OF THE INVENTION

The present invention is summarized in that equipment for holding a serum container or the like includes a hanger fixed to a ceiling by fasteners, a bolt linking the hanger to a rotatable tubular structure with a nylon washer to reduce friction therebetween during rotational movement, a retainer set of a steel dented washer, a second nylon washer and a steel washer being tightened to keep the hanger and the tubular structure together.

Other objects and advantages will become apparent from the following description taken in connection with the accompanying drawings.

DETAILED DESCRIPTION

Figure 1:
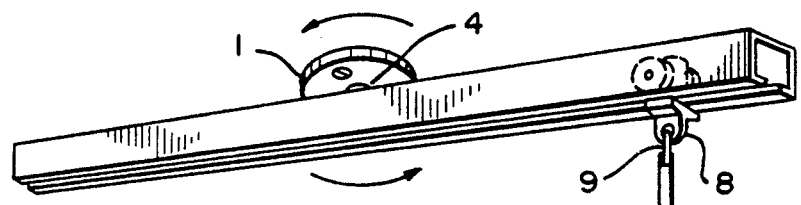
FIG. 1 is perspective view of equipment for suspending a device from an overhead position in accordance with the present invention.
Figure 2:
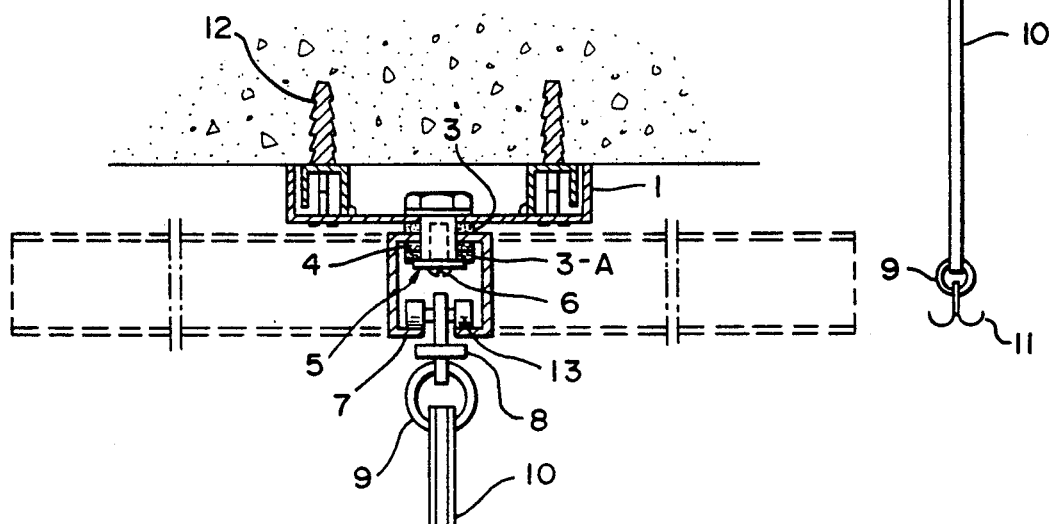
FIG. 2 is a cross-sectional view of FIG. 1.
Figure 3:
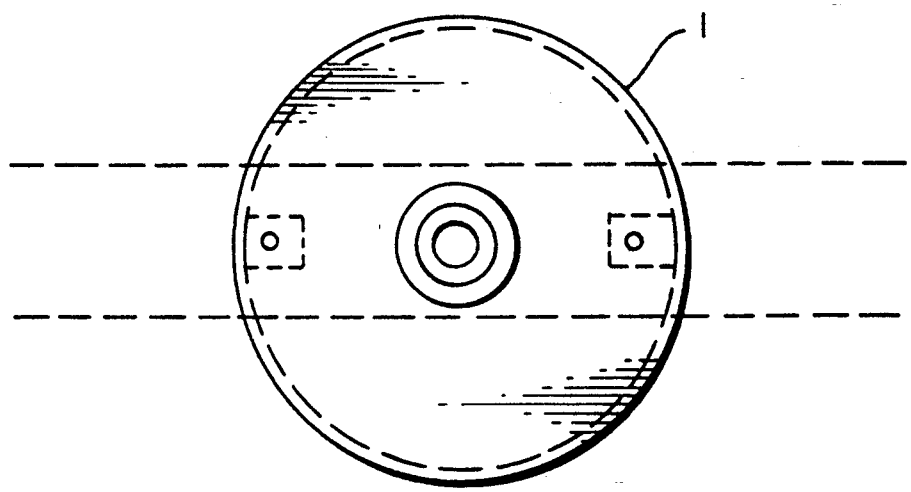
FIG. 3 is a partial top plan view of a detail of FIG. 1.
Figure 4:
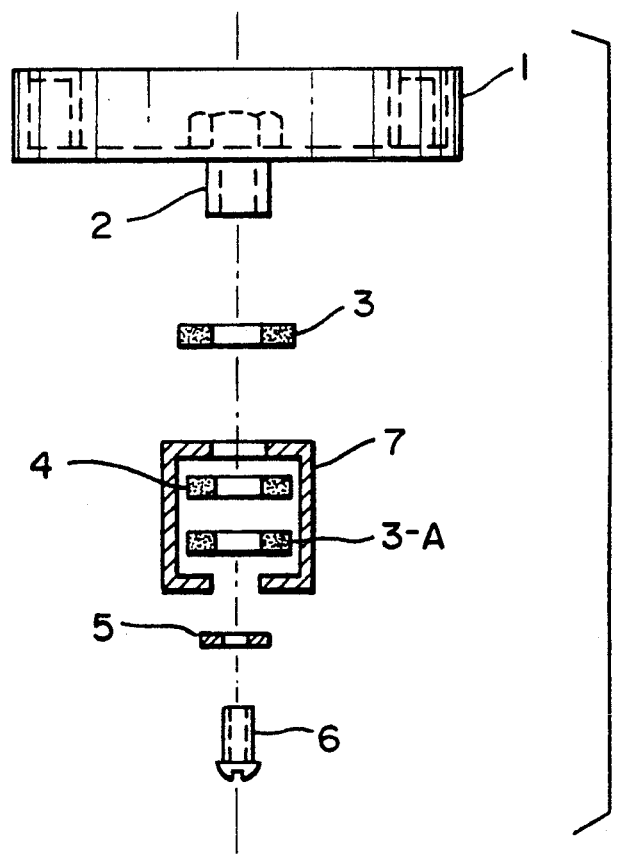
FIG. 4 is a partial exploded view of FIG. 3 with parts in section.

As is shown in FIG. 1, the present invention includes overhead suspension equipment including a cylindrical hanger 1 fixed to a ceiling of a vehicle or a room by means of fastening screws 12.

The center of the hanger 1 has a hole to anchor the head of bolt 2 which, along with screw 6, gathers nylon washer 3, steel dented washer 4, nylon washer 3-A and steel washer 5, and fasten them together.

Washer 3 is positioned between hanger 1 and tubi structure 7 to reduce friction when rotational mo ment of structure 7 in relation to hanger 1 occurs.

A sliding unit 8 includes a pair of wheels 13 running longitudinally within tubular structure 7 and carries vertical stem 10 through longitudinal slot cut in lower face of the tubular structure 7. Vertical stem 10 has a ring 9 in its upper end and a similar ring 9 in its lower end, this one carrying a hook 11 to hold a serum container (not shown in the drawings). Rings 9 and 9 facilitate the movement of stem 10, along with serum container, to every new position, as operated by the patient or medical attendant.

Therefore, the equipment of the invention permits the serum container to have circular movements, accompanying rotation of tubular structure 7, straight movements whenever unit 8 travels lengthwise within slot of tubular structure 7, and combined movements as well, thereby providing prompt following of the serum container to any movement of the patient.

Figures 5, 6:
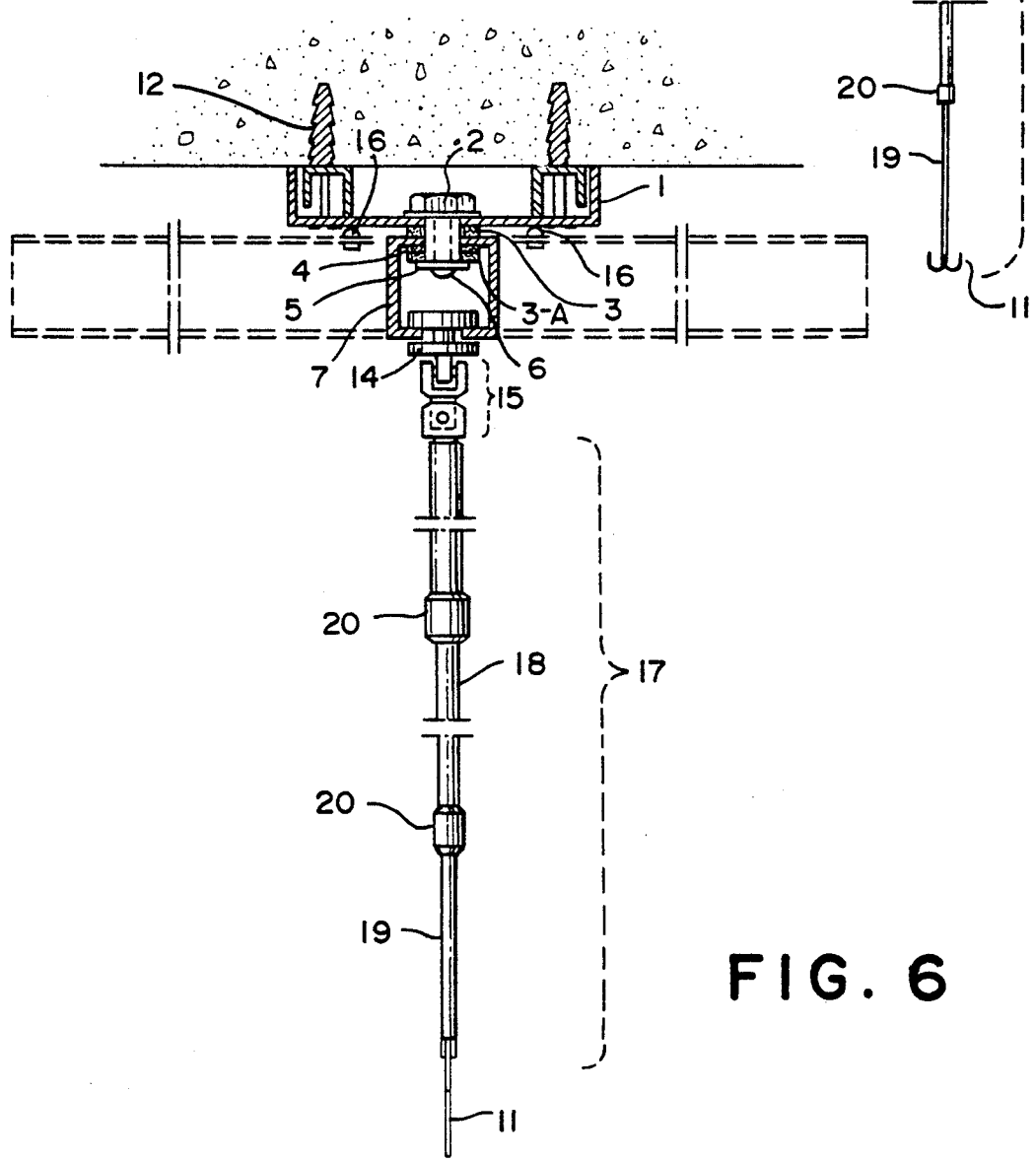
FIG. 5 is a perspective view similar to FIG. 1 but showing a telescopic stem.
FIG. 6 is a cross-sectional view of FIG. 4.

Additional features are shown in FIGS. 5 and 6 wherein with respect to the rotational tubular structure 7, two supports 16 have been installed in the upper face of the element 7 in order to avoid tilting of structure 7 whenever a sliding vertical stem structure 17 approaches one of the ends of tubular element 7.

The sliding unit includes a slider 14 capable of traveling in the slot of the tubular structure 7, as depicted in FIG. 6. A universal joint 15 includes two U-shaped elements, each having a base plate and two spaced parallel legs extending therefrom with an axle-like pin extending between such two parallel legs; the two pins are disposed in crosswise relation to each other while the two legs of one U-shaped element are positioned 90° to the two legs of the other U-shaped element. Accordingly, the universal joint 15 enables tilted movement of the telescopic stem 17 to any direction, as pulled by the user, thereby permitting a serum container to follow easily the new positions of the patient. Slider 14, being in the form of a spool, is also capable of rotating within tubular structure 7.

Stem 17 is a telescopic structure with a hook 11 (to hold a serum container) in its lower end. The serum container may be kept at any height by way of eccentric means acting on telescoping parts 18 and 19. FIG. 6 depicts a three-part stem 17 having nylon sleeves 20 to reduce noise and friction among telescopic components.

Inasmuch as the present invention is subject to many variations, modifications and changes in detail, it is intended that all matter contained in the foregoing description or shown in the accompanying drawings shall be interpreted as illustrative and not in a limiting sense.

I claim:

1. Equipment for holding a serum container comprising
    a hanger (1),
    fasteners (12) for fixing said hanger (1) to a ceiling,
    a rotatable tubular structure (7),
    bolt means (2) linking said hanger (1) to said rotatable tubular structure (7),
    a non-friction washer (3) operatively positioned on said bolt means (2) between said hanger (1) and said rotatable tubular structure (7) to reduce friction during relative rotational movement between said hanger (1) and said rotatable tubular structure (7),
    means for keeping said hanger (1) and said rotatable tubular structure (7) together including a first dented washer (4), a second washer (3-A), a third washer (5) and a screw (2) in said bolt means (2) supporting said first, second and third washers (4, 3-A, 5) together as a unit with said hanger (1) and said rotatable tubular structure (7), sliding means supported by said rotatable tubular structure (7), vertically disposed tube means connected to said sliding means and adapted to carry a serum container.

2. Equipment for holding a serum container according to claim 1 wherein said rotatable tubular structure (7) has a longitudinal slot in its lower face, said slider means includes a slider unit traveling in said slot and carrying said tube means, said tube means having a vertical stem portion (10) and rings (9, 9) respectively, in upper and lower ends of said vertical stem portion (10), lower ring (9) having a hook (11) to hold a serum container.

3. Equipment for holding a serum container according to claim 1 wherein said rotatable tubular structure (7) has a longitudinal slot in its lower face, said slider means includes a slider (14) capable of rotating and sliding within said rotatable tubular structure (7) in order to follow movements by said tube means and said rotatable tubular structure (7), a universal joint (15) operatively disposed between said tube means and said slider (14), and said tube means including a telescopic stem (17) having two telescopic components (18, 19) and a hook (11) on its lower end to carry a serum container and having eccentric means (20) engaging adjacent portions of said components (18, 19) for adjusting the hook (11) to desired heights.

4. Equipment for holding a serum container comprising a hanger (1) adapted to be secured to an overhead supporting structure, a rotatable tubular element (7) disposed adjacent said hanger (1), bolt means (2) on said hanger (1) extending into said tubular element (7), a first washer (3) on said bolt means (2) between said hanger (1) and said tubular element (7) to reduce friction during rotation of said tubular element (7) relative to said hanger (1), a second washer (4) on said bolt means (2) abutting said tubular element (7), a third washer (3-A) on said bolt means (2) abutting said second Washer (4), a fourth washer (5) on said bolt means (2) abutting said third washer (3-A), fastener screw means (6) extending into said bolt means (2) and having a head portion abutting said fourth washer (5) whereby all four washers are secured onto said bolt means (2),. sliding means carried by said tubular element (7) for sliding movement therebetween, and tube means having an upper connection with said sliding means and a lower connection adapted to hold a serum container.

* * * * *